United States Patent [19]

Schwab

[11] Patent Number: 5,121,061
[45] Date of Patent: Jun. 9, 1992

[54] PHASE CORRECTION FOR STREAMING CURRENT SIGNAL

[75] Inventor: George M. Schwab, Philadelphia, Pa.

[73] Assignee: Milton Roy Company, St. Petersburg, Fla.

[21] Appl. No.: 568,205

[22] Filed: Aug. 16, 1990

[51] Int. Cl.⁵ .................. G01N 27/60; H03K 5/153
[52] U.S. Cl. .................. 324/453; 324/447; 307/354
[58] Field of Search .............. 324/453, 447, 438, 439, 324/444, 446, 450, 452; 134/1, 143, 184; 204/193, 280; 307/354, 269; 328/201, 63, 72

[56] References Cited

U.S. PATENT DOCUMENTS

| | | |
|---|---|---|
| 3,368,145 | 2/1968 | Gerdes ...................... 324/453 |
| 3,369,984 | 2/1990 | Gerdes ...................... 204/400 |
| 3,399,133 | 8/1968 | Gerdes et al. ............... 210/709 |
| 3,470,465 | 9/1969 | Wuschke .................... 324/709 X |
| 4,010,386 | 3/1977 | Rosselle .................... 307/354 X |
| 4,446,435 | 5/1984 | Canzoneri ................... 324/453 |
| 4,535,295 | 8/1985 | Kokuryo .................... 307/354 X |
| 4,825,169 | 4/1989 | Carver ...................... 324/453 |
| 4,922,757 | 5/1990 | Rozelle et al. ............... 307/354 X |
| 4,968,902 | 11/1990 | Jackson ..................... 307/354 X |

Primary Examiner—Kenneth A. Wieder
Attorney, Agent, or Firm—Woodcock Washburn Kurtz Mackiewicz & Norris

[57] ABSTRACT

In a streaming current signal, a zero crossing circuit tracks the phase of the streaming current signal. A latch is clocked in response to the outputs of the zero crossing signal to compensate the piston direction signal for change of phase of the streaming current signal.

6 Claims, 2 Drawing Sheets

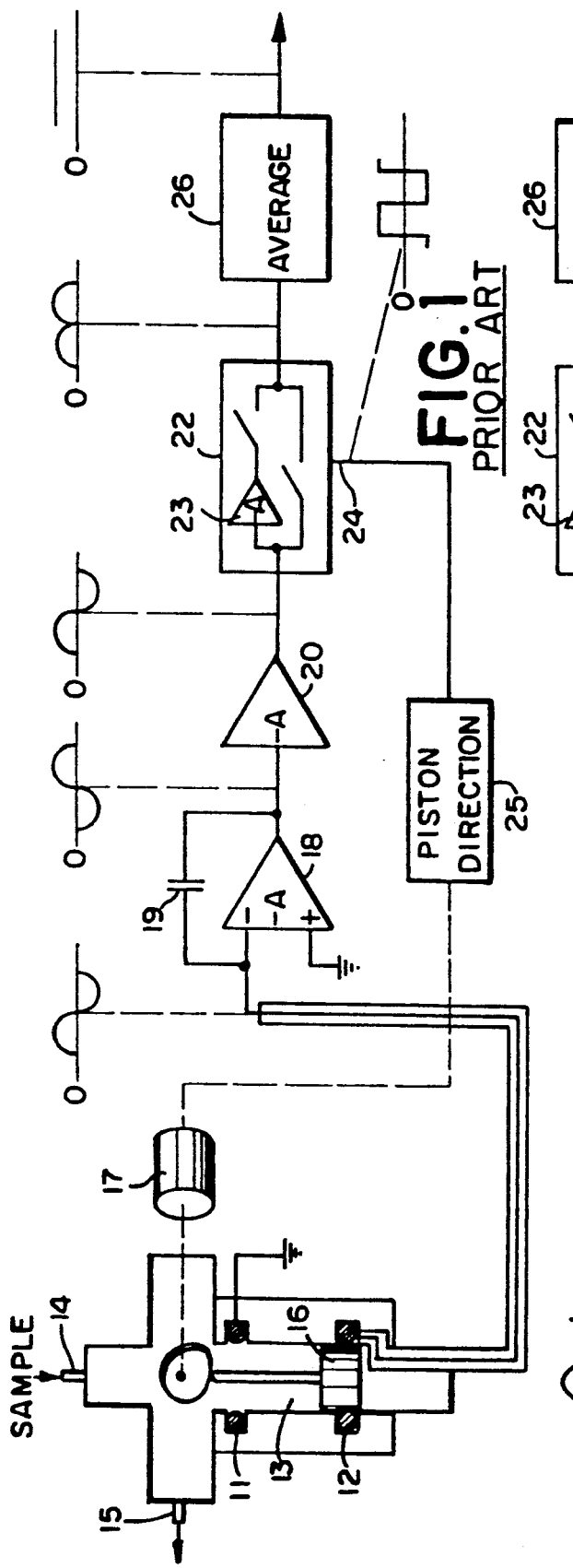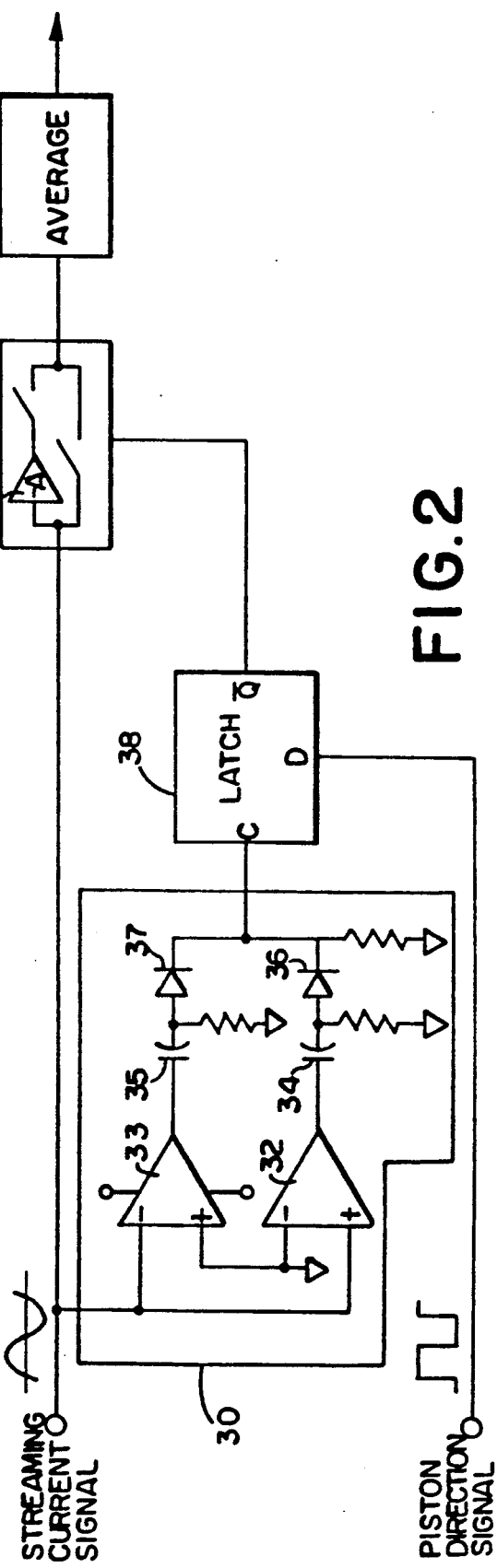

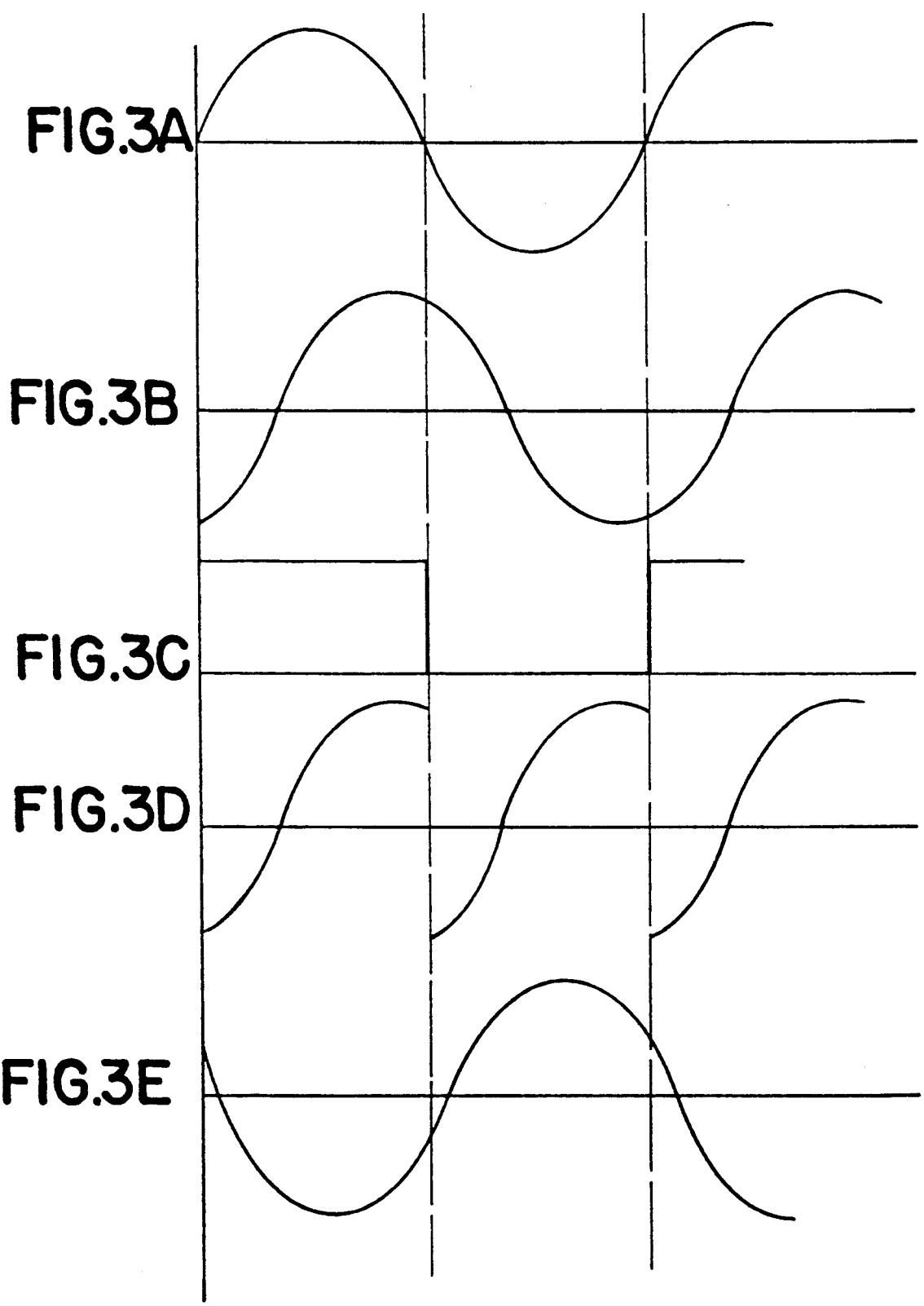

PHASE CORRECTION FOR STREAMING CURRENT SIGNAL

BACKGROUND OF THE INVENTION

This invention relates to streaming current detectors, and more particularly, to correcting for the change of phase in a streaming current signal.

General Background

Streaming current detectors measure the charge on particles in a fluid sample stream.

U.S. Pat. Nos. 3,368,144, 3,368,145-Gerdes and 3,369,984, and 3,911,133-Gerdes, et a], show streaming current detectors. U.S. Pat. No. 4,446,435-Canzoneri and U.S. Pat. No. 4,825,169-Carver show improvement on the streaming current detector.

In the instruments shown and described in these patents, a reciprocating measuring piston moves a sample fluid past measuring electrodes which produce a streaming current signal.

SUMMARY OF THE INVENTION

We have found that the streaming current signal can change phase in relation to the piston position. This change in phase is related to capacitance and/or colloidal density in the sample stream. Changes in phase cause a change in the output value of the instrument without regard to the actual streaming current value. In accordance with the present invention, the phasing problem in streaming current detectors is corrected so that it does not lead to errors in the measured values of streaming current. This is quite significant for waste water and industrial applications.

In accordance with the present invention, a zero crossing circuit tracks the phase of the streaming current signal. A sensor produces a piston direction signal related to the direction of motion of the piston. This piston direction signal is compensated for in response to the output of the circuit which tracks the phase of the streaming current signal. In this manner, the error which otherwise would be introduced by phase change is eliminated.

The foregoing and other objects, features and advantages of the invention will be better understood from the following more detailed description and appended claims.

SHORT DESCRIPTION OF THE DRAWINGS

FIG. 1 shows a typical streaming current detector;
FIG. 2 shows the compensating circuit of the present invention; and
FIG. 3A–FIG. 3E are waveforms depicting the operation of the invention.

DESCRIPTION OF THE PREFERRED EMBODIMENT

FIG. 1 shows a typical streaming current detector. A pair of electrodes 11 and 12 are disposed in a bore 13. Sample fluid flows through inlet 14 and outlet 15. A piston 16 reciprocates in the bore between electrodes 11 and 12, thereby pushing sample fluid past the electrodes first in one direction and then in the other direction. A motor 17 has a shaft connected to an eccentric or the like which reciprocates the piston 16 in the bore.

Electrodes 11 and 12 are connected through coaxial cable to the amplifying circuitry which includes operational amplifier 18. The output of operational amplifier 18 is further amplified in amplifier 20, the output of which is applied to the input of rectifier 22. Rectifier 22 is an electronic synchronous detector which includes operational amplifier 23. The output signal from amplifier 20 is directed to both the inverting and non-inverting inputs of operational amplifier 23. Electronic switches consisting of field effect transistors are appropriately connected to a control port 24 through which the selection of inverting or non-inverting amplification can be made by remote electrical signals.

The control port 24 of rectifier 22 is connected to the output of piston direction generator 25 which may typically be the light detector and light source shown in the Carver U.S. Pat. No. 4,825,169. Piston direction generator 25 generates a piston direction signal in synchronism with the reciprocation of piston 16.

The output of rectifier 22 is applied to an averaging circuit 26 which produces an output proportional to the charge of the sample fluid.

Referring to FIG. 2, the streaming current signal is applied to means for tracking the phase of the streaming current signal which includes the zero crossing circuit 30. Zero crossing circuit 30 includes operational amplifiers 32 and 33, associated capacitors 34 and 35, and diodes 36 and 37. Zero crossing circuit 30 produces a pulse each time the streaming current signal crosses through zero. That is, amplifier 33, capacitor 35 and diode 37 produce a high voltage signal when the streaming current signal crosses through zero in the positive direction, and inverting amplifier 32, capacitor 34 and diode 36 produce a low voltage signal when the streaming current signal crosses through zero in the negative direction. These voltage signals are applied to the clock input of a latch 38.

The piston direction signal is produced as before. For example, the light source detector and rotating shutter of the Carver '169 patent are a sensor which produces a signal related to the direction of motion of the piston. The signal may be a square wave which is positive when the piston is moving upwardly and negative when the piston is moving downwardly. The piston direction signal is applied to the D input of latch 38. The latch 38 is clocked by the pulses from zero crossing circuit 30 in a manner which compensates the piston direction signal for change of phase of the streaming current signal.

The latch 38 applies a negative signal to the rectifier 22 when the streaming current signal is in the positive phase, and applies a positive signal to the rectifier 22 when the streaming current signal is in the negative phase. A positive signal to the rectifier 22 closes a switch to the inverting operational amplifier 23 while a negative signal closes a switch to the non-inverting circuit. Thus, the negative portion of the streaming current signal is inverted, and the resulting signal consists of the two positive portions of the sinusoidal signal. This converted signal is fed into the average circuit 26.

Timing of signal change to the rectifier 22 is crucial to accurate averaging of the streaming current. The prior art as disclosed in the Carver '169 patent utilized the optical switch which is directly linked to the piston movement. The shutter or disk is directly mounted on the motor shaft that drives the piston so that the light emitted by the light source reaches the sensor only when the piston is moving in one direction to activate the switch.

This mechanical synchronization to determine when to send a positive or negative signal to the rectifier 22 has inherent inaccuracy. One source of inaccuracy was found to exist in the capacitance of the particles in the sample fluid. Due to this capacitance, the changes in electrical charge measured by the electrodes are not completely synchronized with the direction of the piston travel. The change in electrical charge in fact lags behind in time after the piston starts to travel in one direction because the change in electrical charge initially charges the surface of particles in the sample fluid.

The phase shift in the measured current causes an inaccurate reading. FIG. 3A shows a hypothetical streaming current detected by the electrodes 11 and 12. FIG. 3C is a square wave generated by the optical switch disclosed by the Carver '169 patent. The positive phase of the square wave indicates the downward motion of the piston, and the corresponding positive phase of streaming current during this motion is in perfect synchronization. That is, the start and end of the positive square wave match the zero crossing of the sinusoidal wave. In reality, the capacitance in the sample fluid causes a lag in rise and fall of the streaming current signal as shown in FIG. 3B. When the out-of-phase square wave is fed into the rectifier 22, the streaming current signal in FIG. 3D results. Thus, when the signal in FIG. 3D is fed into the averaging circuit 26, the negative portion of the signal cancels the positive portion and the output from averaging circuit 26 is much lower than the actual streaming current.

The present invention improved the accuracy by synchronizing the movement of the piston with its corresponding stream current. As described above, in FIG. 2 the zero crossing circuit 30 generates a positive signal when the streaming current crosses from the negative to positive. The positive input to C in the latch 38 starts the clock in the latch 38. If input D in 38 is positive while the clock is running (i.e. the direction of the piston movement is downward), the latch output sends a negative signal to the rectifier 22. The latch 38 maintains the negative output until the clock is reset by a negative signal to C in the latch 38. When the streaming current crosses zero from positive to negative, the zero crossing circuit 30 generates a negative signal and resets the latch 38. Thus, the output from the latch changes to positive and remains until the start of another cycle of the streaming current signal. In effect, by inverting only the negative phase of the streaming current signal, the zero crossing circuit 30 and the latch 38 correctly adjusted the phase shift between the signal representing the direction of the piston movement and the streaming current detected by the electrodes.

The latch mechanism works for most sample fluids to correct the phase difference. Because the amount of capacitance in the sample fluid is unknown, it is hypothetically possible to have a sufficiently large capacitance to cause the streaming current to be out-of-phase by over 180 but less than 360 degrees as shown in FIG. 3E. This situation would result in a reversed polarity voltage reading. However, from our experiments such huge out-of-phase situation does not occur because the capacitance in most samples is limited.

While a particular embodiment of the invention has been shown and described, various other modifications are within the true spirit and scope of the invention. The appended claims are, therefore, intended to cover all such modifications.

What is claimed is:

1. A streaming current detector for determining the charge condition in a fluid containing particles which have a capacitance comprising:
   a pair of electrodes disposed in a bore for producing a streaming current signal which may be changed in phase by said capacitance;
   a reciprocating piston;
   means for reciprocating said piston in said bore;
   a sensor producing a piston direction signal related to the direction of motion of said piston;
   tracking means for tracking the phase of said streaming current signal; and
   means responsive to said tracking means for compensating said piston direction signal for change of phase of said streaming current signal caused by said capacitance.

2. The streaming current detector recited in claim 1 further comprising:
   a rectifying stage and an averaging stage for said streaming current signal, said compensating being effective to eliminate the error which would otherwise be introduced by phase change in said rectifying and averaging stages.

3. The streaming current detector recited in claim 1 wherein said tracking means comprises:
   a zero crossing circuit, said streaming current signal being applied to said zero crossing circuit to produce an output each time said streaming current signal passes through zero.

4. The streaming current detector recited in claim 3 further comprising a latch, the output of said zero crossing signal being applied to clock said latch.

5. The streaming current detector recited in claim 4 wherein said piston direction signal controls the state of said latch, which changes in response to said output of said zero crossing signal, the state of said latch being applied to control said rectifying stage.

6. The streaming current detector recited in claim 5 wherein said compensating means ensures that one polarity of rectification is applied to said streaming current signal when said piston is traveling in a first direction and said signal is of one polarity and a different polarity of rectification is applied to said streaming current signal when said piston is traveling in the opposite direction and said signal is of the opposite polarity.

* * * * *